United States Patent

Maurer et al.

[11] 4,212,720
[45] Jul. 15, 1980

[54] ELECTRICALLY HEATED ELECTROCHEMICAL SENSOR CONSTRUCTION, PARTICULARLY TO DETERMINE OXYGEN CONCENTRATION IN EXHAUST GASES FROM COMBUSTION ENGINES

[75] Inventors: Helmut Maurer, Schwieberdingen; Franz Rieger, Aalen-Wasseralfingen; Ernst Linder, Mühlacker; Rainer Schüssler, Bietigheim-Bissingen, all of Fed. Rep. of Germany

[73] Assignee: Robert Bosch GmbH, Stuttgart, Fed. Rep. of Germany

[21] Appl. No.: 919,700

[22] Filed: Jun. 27, 1978

[30] Foreign Application Priority Data

Jul. 20, 1977 [DE] Fed. Rep. of Germany ....... 2732743

[51] Int. Cl.² ............................................. G01N 27/58
[52] U.S. Cl. .................................................. 204/195 S
[58] Field of Search ............................. 204/195 S, 1 S

[56] References Cited

U.S. PATENT DOCUMENTS

| | | | |
|---|---|---|---|
| 2,030,937 | 2/1936 | Reichmann | 123/145 A |
| 2,898,571 | 8/1959 | Moule et al. | 338/238 |
| 3,252,122 | 5/1966 | Baxter | 338/271 |
| 3,546,086 | 12/1970 | Sayles | 204/195 S |
| 3,844,920 | 10/1974 | Burgett et al. | 204/195 S |
| 3,915,828 | 10/1975 | Cleary et al. | 204/195 S |
| 3,928,161 | 12/1975 | McIntyre et al. | 204/1 S |
| 3,999,947 | 12/1976 | Mihara et al. | 23/254 E |
| 4,129,099 | 12/1978 | Howarth | 204/195 S |
| 4,129,491 | 12/1978 | Obiaya | 204/195 S |

FOREIGN PATENT DOCUMENTS 2304464 8/1974 Fed. Rep. of Germany ....... 204/195 S

Primary Examiner—G. L. Kaplan
Attorney, Agent, or Firm—Frishauf, Holtz, Goodman & Woodward

[57] ABSTRACT

An electrical heating element 35, 35' is located in a thin walled, closed metal tube or sleeve 37, 37' which is packed with a packing material 38, 38' of good heat conductive, insulating properties; the electrical heating element is a spirally wound resistance heater embedded in the insulating packing. A solid electrolyte body 11, 68 surrounds at least a portion of the thin walled metal sleeve and is positioned in heat exchange relation therewith. The solid electrolyte body may be a closed tube 11 or may be applied as a ring element 68 over the thin walled metal tube with an insulating material layer 66 interposed.

8 Claims, 3 Drawing Figures

ELECTRICALLY HEATED ELECTROCHEMICAL SENSOR CONSTRUCTION, PARTICULARLY TO DETERMINE OXYGEN CONCENTRATION IN EXHAUST GASES FROM COMBUSTION ENGINES

Reference to related applications, assigned to the assignee of the present application:
U.S. Ser. No, 918,145, filed June 22, 1978, MAURER et al
U.S. Pat. Nos. 3,546,086; 3,597,345.

The present invention relates to an electrochemical sensor, and more particularly to a solid electrolyte oxygen concentration cell used to sense the composition, and especially the oxygen content of combustion exhaust gases, typically the exhaust gases from an internal combustion engine.

BACKGROUND AND PRIOR ART

Ion-conductive solid electrolyte cells are usually made of a material which provides sufficient ion conductivity only when the material has reached a temperature of 400° C. or higher. Below that temperature, the ion conductivity is usually insufficient for practical evaluation. When used in connection with exhaust gases from internal combustion engines, contamination of the cell due to additives in the gases is an additional problem. For example, lead is frequently contained in the exhaust gases. Solid electrolyte cells have to reach a temperature of 500° C. and more before their function is not impaired by lead contained in exhaust gases. For rapid operation under starting conditions, and generally for reliable operation, it has therefore been proposed to provide the sensors with heating elements.

U.S. Pat. No. 3,546,086 describes a sensor which utilizes a reference gas and which is equipped with a heater element, located in the interior of a tubular solid electrolyte body, spaced from the inner wall thereof. Such a construction is expensive to manufacture and not suited for mass production; it is difficult to so construct such an article that it is immune to malfunction due to vibration or shock, frequently encountered in automotive environments. It has also been proposed—see German Disclosure Document DE-OS No. 23 04 464—to utilize electrochemical sensors having ion conductive solid electrolyte bodies which do not require a reference gas.

THE INVENTION

It is an object to so construct a solid electrolyte oxygen concentration cell type sensor that it can be heated, made by mass production assembly, and yet is essentially immune to damage due to vibration, shock, or the like—in short, is suitable for automotive use.

Briefly, a thin walled, closed metal sleeve of good heat conductive insulating material has a heater resistance wire spirally located therein. An insulating packing, preferably in powdery or granular form, is packed in the tube, the insulating wire being embedded in the insulating packing. The thin walled closed metal sleeve, which may form one electrical terminal for the heater wire, is located in heat exchange relation with respect to the solid electrolyte body, forming the ion conduction oxygen concentration cell. It is positioned coaxially within the electrolyte body which is tubular, the inside of which is connected to a reference gas and the outside is exposed to exhaust gases from an internal combustion engine; or by having placed a ring of solid electrolyte material thereover, with interposition of an insulating layer, the ring of solid electrolyte body being ion conductive without requiring a reference gas, the entire assembly being exposed to the gases, the oxygen concentration of which is to be measured.

The sensor has the specific advantage that the construction is sturdy, highly resistant to damage due to vibration, and can be constructed inexpensively, thus being eminently suitable for mass production.

Drawings, illustrating two embodiments of preferred examples, wherein.

The drawings in their original scale are enlarged with respect to an actual sensor suitable for automotive use and made in mass production.

Figure 1:
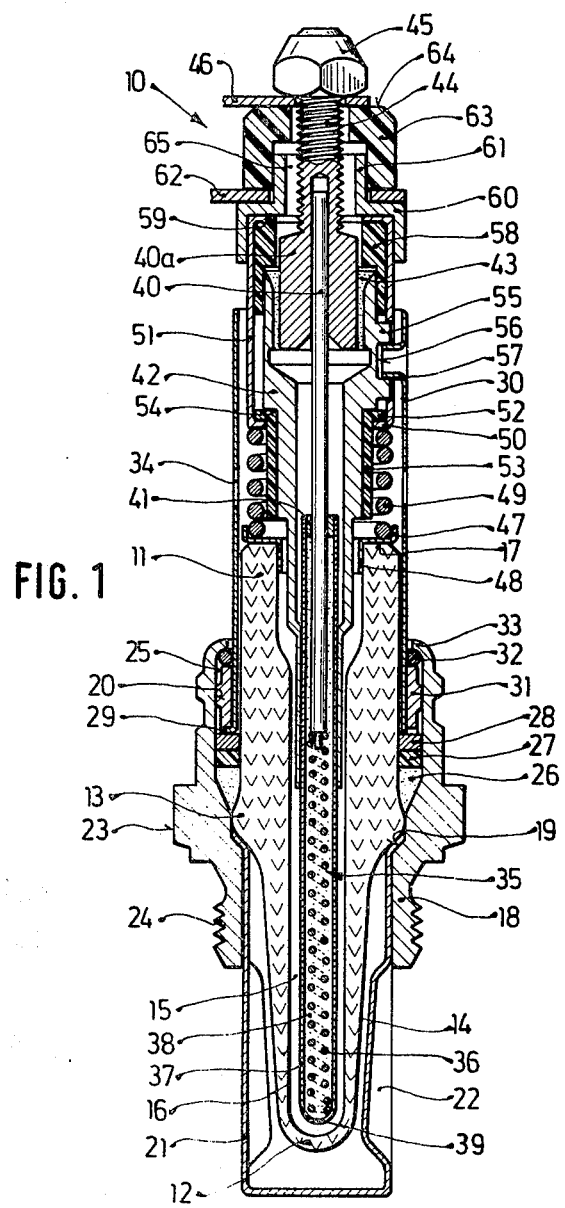
FIG. 1 is a schematic longitudinal section through a sensor utilizing a reference gas.

Embodiment of FIG. 1: The sensor 10 has a solid electrolyte tube 11 made of stabilized cubic zirconium dioxide. It has a closed bottom 12 formed on and integral with the tubular body 11. The end of the body 11 with the bottom 12 extends into an exhaust pipe of an automotive engine, not shown. The other end of the body 11 is formed with a flange 13. The tube 11 is coated with an electron conductive porous layer 14 at its outside, at least in the region of exposure of tube 11 to the exhaust gases. The layer 14 of platinum additionally extends to the region of the shoulder 13 of the solid electrolyte tube 11. A protective layer to protect the platinum coating 14 against mechanical and thermal attack by the exhaust gases has been omitted for simplicity; such a layer may, for example, be a porous coating of magnesium spinel.

The solid electrolyte tube 11 has an electron conductive path 16 located at an interior surface 15 thereof. The path 16 extends into the region of the bottom 12 and, preferably, also consists of platinum. The path 16 extends at the other side or end of tube 11 up to and on the facing end surface 17 of the tube 11.

A housing 18 surrounds the solid electrolyte tube 11 throughout a portion of its length. The housing consists of an electrically conductive material, for example heat resistant steel. The solid electrolyte body 11 is positioned with its flange 13 on an internal shoulder 19 of a longitudinal bore 20 of the housing. The flange 13, pressing against the shoulder 19, additionally clamps a protective tube 21 to the housing which surrounds the portion of the solid electrolyte tube 11 extending into and exposed to the exhaust gases. The protective tube 21 has clearance from the solid electrolyte tube 11 and is formed with inlet and outlet openings 22 to permit a stream of exhaust gases to pass around the solid electrolyte tube 11. The outside of the housing 18 is formed with wrenching surfaces 23, for example like a hexagonal nut similar to a spark plug gripping hexagon, and additionally with a threaded portion 24 to thread the sensor securely and gas-tight into the exhaust pipe of an internal combustion engine (not shown). The housing 23 surrounds the portion of the solid electrolyte tube remote from the flange with clearance to form a ring-shaped space 25. This space or gap 25 is filled with an electrically conductive sealing mass 26, such as, for example, graphite powder, in a region immediately adjacent the flange 13. The graphite powder is in electrical contact with the platinum coating 14 on the solid electrolyte tube as well as with an external electrical electrode, typically the housing 18 itself which, usually, is connected to ground or chassis, or the frame of a vehicle or internal combustion engine. The sealing mass 16 is compressed by an insulating bushing 27 and a metallic washer 28. A peened-over ring 32 is placed on a guide bushing 31, held in position by an inwardly turned edge 33 of the housing 18. Guide bushing 31 locates a metallic protective sleeve 30 which has a lower turned-over edge 29, bearing on washer 28. The protective sleeve 30 is a metallic tube which extends outwardly over the solid electrolyte tube and beyond its terminal facing the end 17. It is formed with one or more air entrance openings 34 to permit reference air to penetrate therethrough.

A heater element 35 extends coaxially into the interior space 15 of the solid electrolyte tube. The heating element 35 essentially entirely fills the inner space, leaving only a small distance to the electrolyte tube 11. The heater element 35 is a resistance heater spiral located within a thin walled metal sleeve 37 and embedded in a packing 38 of electrically insulating but good thermally conductive material, for example magnesium oxide. The metal sleeve 37, for example of a CrAl alloy has a closed bottom 39 located close to the bottom 12 of the solid electrolyte body 11. The bottom 39 forms a weld point for one end of the resistance wire spiral 36. A connecting bolt 40 for the heater element 35 extends into the open end portion of the metal sleeve 37. The bolt 40 is connected to the second end terminal of the resistance wire spiral 36, for example by welding. The terminal side of the metal sleeve 37 is closed off by an electrically insulating sealing ring 41 which prevents loss of the powder or pulverized packing material 38; sealing ring 41 is secured in the metal sleeve 37 by peening over or rolling over the edge of the metal sleeve 37. The end portion of the metal sleeve 37 is press-fitted in the end portion of an intermediate sleeve 42 and held therein; the connecting bolt 40 is press-fitted to a connecting terminal 40a. Terminal 40a is secured in a second end portion of the intermediate sleeve 42 by an electrically insulating glass melt 43, or by a pinch or melt seal. The connecting terminal 40a is threaded with a thread 44 at its end terminal to which a connecting nut 45 is screwed to secure a connecting bus 46 for the heater element 35.

The heater element 35 including the connection or terminal elements 40, 40a and 45 are held in the assembly by a metallic washer 47 located on the facing end surface 17 of the solid electrolyte body 11. The washer 47 is positioned with respect to the interior space 15 of the solid electrolyte body by a tubular extension 48 which is spaced from the intermediate tube 42. A compression spring 49 engages the washer 47, the other end of compression spring 49 engaging the flange 50 of a terminal strip 51. A flange 50 of strip 51 engages around a flange 52 of an insulating bushing 53 which is located to surround a portion of the sleeve 42 and which engages a shoulder 54 of the sleeve 42. The counter bearing surface for the compression spring 49 is formed by three internal projections 55 of the sleeve 42. Each one of the projections 55 defines grooves 56 therebeneath into which internally extending projections 57, formed on protective sleeve 30, can project and engage.

The conductive strip 51 is supported with respect to the sleeve 42 by an insulating part 58 which terminates in an internally extending ring 59. A metallic connection bushing 60 is located on the portion 59 to which a connecting bus 62 extends to permit electrical connection for the sensing signal from the sensor 10, by connection with the sleeve portion 61 of the bushing 60. An insulating bushing 63 is located on the sleeve portion 61 to support, in insulated relation, the connecting bus 46 for the heater element 35. A ring-shaped gap 65 separates the tubular portion 61 of the bushing 60 from the connecting end 40a of the heater element 35.

Sensing circuit: Connecting bus 62—contact bushing 60—connecting strip 51—compression spring 49—washer 47—platinum path 16; solid electrolyte tube 11; platinum path 14—conductive sealing mass 26—sensor housing 18, connected to chassis or ground.

Heater circuit: Connecting bus 46—terminal 40a, connecting bolt 40; resistance wire spiral 36; metal sleeve 37—intermediate sleeve 42—internal projection 57 of protective sleeve 30—protective sleeve 30—metal washer 28—housing 18, connected to ground or chassis.

Reference air can penetrate through the openings 34 and into the interior of the body 11 in the space between the inner wall of body 11 and the outer surface of the heater tube 37.

Figure 2:
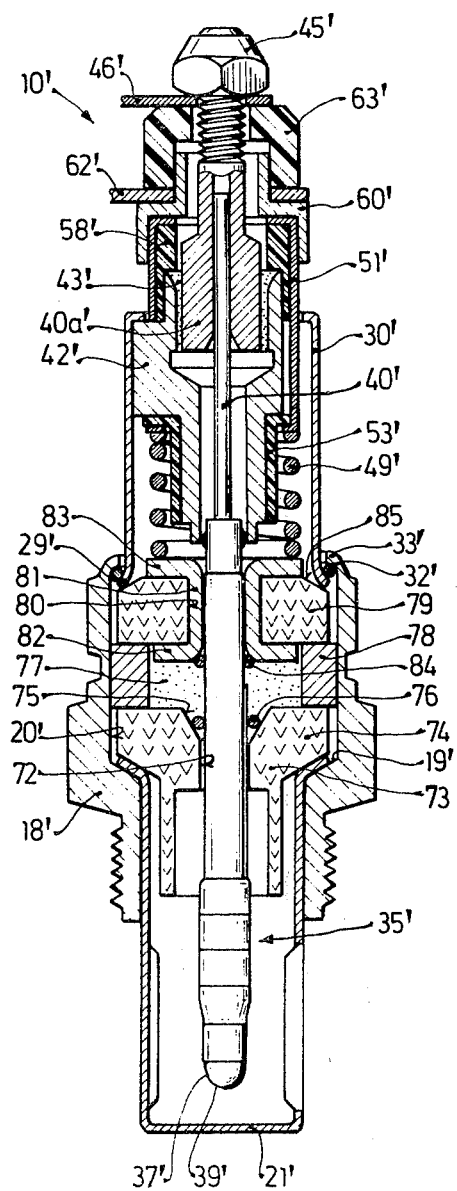
FIG. 2 is a schematic longitudinal section through a sensor which does not require a reference substance, and in which the solid electrolyte body and the electrodes are supported by the heater element.
Figure 3:
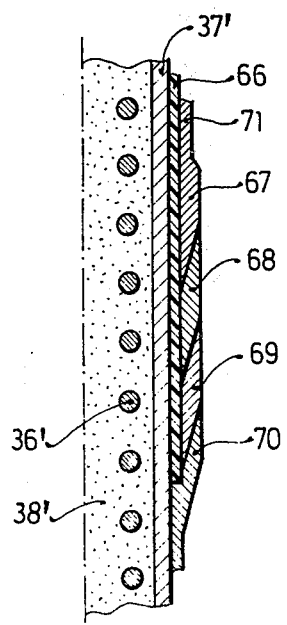
FIG. 3 is a fragmentary longitudinal section view through one side of the sensing element of FIG. 2, to a greatly enlarged scale.

Embodiment of FIG. 2, with reference also to FIG. 3: The sensor 10' also uses a solid electrolyte oxygen concentration cell having an ion conductive solid electrolyte. The cell differs from the cell of FIG. 1, however, in that an additional reference substance, such as the oxygen of the air, is not needed. The sensor 10' has a heating element 35' which corresponds, generally, to the heating element 35 of FIG. 1. Components similar to those of FIG. 1 have been given the same reference numerals, with a prime notation. A resistance wire spiral 36' is enclosed in a packing of powder or pulverized material or granular material 38', enclosed in a metal sleeve 37', and electrically connected to a connecting bolt 40' which terminates in an end head 40a, the bolt being electrically connected to a connection nut 45' and, then, to the connecting bus 46'. The following elements are also comparable to those of the sensor 10 of FIG. 1: The insulating sleeve 63', the connecting sleeve 62' for the sensing signal, the contact element 60', the connecting strip 51', the insulator 58', the glass melt lead-through 43', sleeve 42', insulating sleeve 53', compression spring 49', protective sleeve 30', the housing 18' with the peened-over ring 32' and the protective sleeve 21'. These elements need not be described again since they are generally similar to those of FIG. 1.

The thin walled metal sleeve 37' retaining the heating element of the sensor 10' is coated at its outer surface with an electrically insulating layer 66 which covers the sleeve 37' except for the end portions. The terminal end portion of the sleeve 37' is press-fitted into the intermediate sleeve 42' and/or connected to the sleeve 42' by welding. The insulating layer 66 is about 0.3 mm thick and located in the region in which the heating element 35' is located. A ring 67 made of a catalytically acting electrically conductive material, such as platinum, is located on the insulating layer 66 in the region of the heating element 35'. This ring is approximately 0.4 mm thick and about 4 mm wide. The ring 67 is joined, in direction to the bottom 39' of the sleeve 37', by a ring 68 made of solid electrolyte material, also approximately 4 mm wide (see FIG. 3). The solid electrolyte is, for example, zirconium dioxide, and so arranged that it partially overlaps the ring 67, as best seen in the half-section of FIG. 3. A ring 69 made of an electrically conductive but catalytically non-active material, such as gold, joins the solid electrolyte ring 68. The gold ring 69 is so constructed that it partially overlaps the solid electrolyte ring 68. Rings 67, 68, 69, together, form the actual measuring instrument. Such a measuring instrument is described, for example, in German Disclosure Document DE-OS No. 23 04 464. The gold ring 69 is connected by an electrically conductive path 70 with the portion of the sleeve 37' which is not covered with the insulating layer 66—see FIG. 3. The platinum ring 67 is connected to an electrically conductive path 71 which may be platinum or gold and which is applied above the insulating layer 66 extending in the direction towards the connecting end of the sensor 10'. Rings 67, 68, 69 can be covered by additional protective coatings which, however, do not form part of the present invention. Serial connection of a plurality of ring assemblies formed of rings 67, 68, 69, all placed on the insulating coating 66, can be used to increase the sensor signal by a corresponding factor. The insulating layer applied to the metal sleeve 37 preferably is a ceramic, such as aluminum oxide—$Al_2O_3$.

The heater element 35' is guided within the housing 18' in the longitudinal bore 72 of an insulating ring 73, preferably made of ceramic, which abuts on the protective tube or sleeve 21' with a head portion 74. The protective tube or sleeve 21', in turn, is engaged by shoulder 19' formed in the longitudinal bore 20' of the housing 18'. The longitudinal bore 72 of the insulator is extended in funnel shape as seen at 75 at the side facing the terminal end of the sensor, and is sealed with a sealing ring 76 located in the expanded section of the funnel-shaped opening. Sealing ring 76 prevents penetration of an electrically conductive elastic packing of graphite 77 located at the upper side thereof—with respect to FIG. 2—and prevents penetration of graphite into the portion of the sensor 10' which is directed towards the exhaust gases. The elastic packing 77 forms an electrical terminal for the conductive path 71 which terminates within the region of the packing 77 on the insulating layer 66 located at the outer sleeve of the heater element 35'. The elastic packing 77 is separated from the housing 18' by an electrically insulating elastic ring 78 located at the inside of the housing 18', the ring, preferably, being made of asbestos. The elastic ring 78 supports a second insulating ring 79 formed similar to a washer and having a central bore 80. A conductive bushing 81 having lower and upper flanges 82, 83 is surrounded by the ring 79; thus, flange 82 forms a conductive connection to the elastic packing 77. The bushing 81 fits over the insulating layer 66 of the heater element 35' and serves as a guide element for the heater element 35'—solid electrolyte support combination 35'. The lower flange 82 of the bushing 81 is sealed by a sealing ring 84 which seals off the gap between the metal sleeve 37' of the heater element—sensor element support tube 37' with respect to the elastic packing 77. The upper flange 83 of the bushing 81 is used as a counter bearing for the compression spring 49'. The surface 85 of the insulating ring 79 supports the peened-over edge 29' of the protective sleeve 30'; the rolled or peened-over edge 33' then secures the entire housing unit together with the intermediate interposition of a peened-over ring 32'.

Path of heater current: Connecting bus 46'—connecting head 40a'—connecting bolt 40'; resistance wire spiral 36'; metal sleeve 37'—intermediate sleeve 42'—protective sleeve 30'—peened-over ring 32'—housing 18', connected to chassis, ground or frame.

Current path for the sensing signal: Connecting bus 62'—contact sleeve 60'—connecting strip 51'—compression spring 49'—bushing 81—elastic packing 77—conductive path 71—platinum ring 67; solid electrolyte ring 68; gold ring 69—conductive path 70—heater element metal sleeve 37'—intermediate sleeve 42'—protective sleeve 30'—peened-over ring 32'—housing 18', connected to ground, chassis or frame.

Neither of the rings 67, 69, not the solid electrolyte body 68 need be formed in ring shape; other configurations can be used, for example partial surfaces, sector-shaped surfaces, or the like. If a plurality of combinations 67-68-69 are serially connected then, of course, the current path above given will be modified by extending, serially, through a plurality of such combinations of catalytically active material 67—solid electrolyte material 68—connecting material 69—and another sequence of elements 67, 68, 69.

In a typical example, the tube 37, 37' is made of a CrAl 25-5 alloy, of about 0.5 mm wall thickness and, in the embodiment of FIG. 1, of about 3 mm diameter; in the embodiment of FIG. 2 about 5 mm diameter. In the embodiment of FIG. 2, the insulating layer 66 is, for example, of alumina material, about 0.3 mm thick.

Various changes and modifications may be made, and features described in connection with any one of the embodiments may be used with any other, within the scope of the inventive concept.

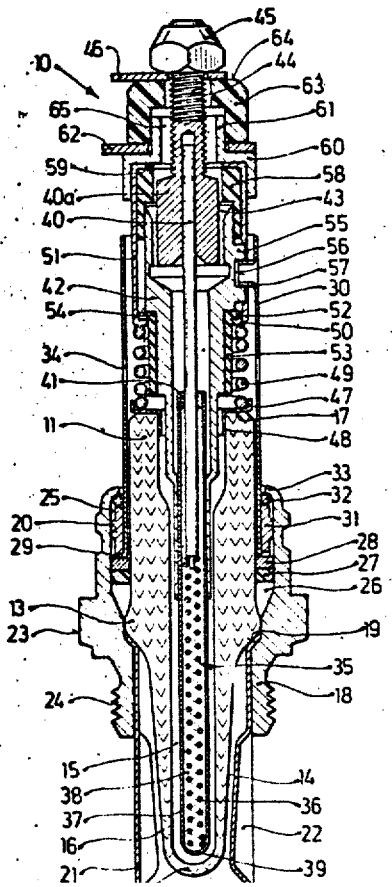

We claim:

1. Electrically heated electrochemical sensor to determine the oxygen concentration in gases, particularly in combustion exhaust gases, especially from internal combustion engines, comprising the combination of
   a housing (18);
   a tubular solid electrolyte body (11, 68) secured in the housing; with
   an electrical heating element (35, 35') in heat exchange relation with the solid electrolyte body which comprises
   a thin-walled, closed metal sleeve (37, 37') coaxially located internally within said body;
   a good heat conductive, electrically insulating material (38, 38') packed in the sleeve;
   and a resistance wire spirally located within the tube and embedded in said insulating packing.

2. Sensor according to claim 1, wherein said heat conductive insulating packing is in powdery, pulverized or granular form.

3. Sensor according to claim 2, wherein said insulating packing comprises magnesium oxide.

4. Sensor according to claim 1 or 2, wherein said spirally wound resistance wire (36, 36') is electrically connected to the closed end (39, 39') of the metal sleeve (37, 37').

5. Sensor according to claim 1 or 2, wherein (FIG. 1) the solid electrolyte body is a tube which is closed at one end.

6. Sensor according to claim 1, wherein (FIGS. 2, 3) the solid electrolyte body comprises a ring (68) located on the outside of the metal sleeve (37');
   an electrically insulating layer (66) interposed between the metal sleeve (37') and the ring of solid electrolyte material (68);
   ring-shaped electrodes (67, 69) in engagement with the solid electrolyte body (68) and located over the electrically insulating layer (66);

and connecting paths (70, 71) in electrical connection with the ring electrodes.

7. Sensor according to claim 6, wherein the solid electrolyte body is a ring having, in cross section, essentially parallelogram configuration, the electrodes (67, 69) having engagement surfaces matching the inclined parallelogram surfaces of the ring-shaped solid electrolyte body (68).

8. Electrically heated electrochemical sensor to determine the oxygen concentration in gases, particularly in combustion exhaust gases, especially from internal combustion engines, having
   a housing;
   an electrical heating element secured to the housing, said heating element comprising
   a thin-walled closed metal sleeve (37');
   a good heat-conductive electrically insulating material (38') packed in the sleeve;
   a resistance wire spirally located within the tube and embedded in insulating packing;
   a layer of solid electrolyte material (68) located at the outside of the metal sleeve (37');
   an insulating layer (66) interposed between the layer of solid electrolyte material (68) and the metal sleeve (37');
   and electrodes (67, 69) and connecting paths (70, 71) located at the outside of the insulating layer (66) over the outside of the metal sleeve (37').

* * * * *

UNITED STATES PATENT AND TRADEMARK OFFICE
CERTIFICATE OF CORRECTION

PATENT NO. : 4,212,720

DATED : July 14, 1980

INVENTOR(S) : Helmut Maurer, et al

It is certified that error appears in the above—identified patent and that said Letters Patent is hereby corrected as shown below:

The title page should be deleted to appear as per attached.

*Signed and Sealed this*

*Seventh* Day of *April 1981*

[SEAL]

Attest:

RENE D. TEGTMEYER

*Attesting Officer*  *Acting Commissioner of Patents and Trademarks*

United States Patent [19]

Maurer et al.

[11] 4,212,720
[45] Jul. 15, 1980

[54] ELECTRICALLY HEATED ELECTROCHEMICAL SENSOR CONSTRUCTION, PARTICULARLY TO DETERMINE OXYGEN CONCENTRATION IN EXHAUST GASES FROM COMBUSTION ENGINES

[75] Inventors: Helmut Maurer, Schwieberdingen; Franz Rieger, Aalen-Wasseralfingen; Ernst Linder, Mühlacker; Rainer Schüssler, Bietigheim-Bissingen, all of Fed. Rep. of Germany

[73] Assignee: Robert Bosch GmbH, Stuttgart, Fed. Rep. of Germany

[21] Appl. No.: 919,700

[22] Filed: Jun. 27, 1978

[30] Foreign Application Priority Data

Jul. 20, 1977 [DE] Fed. Rep. of Germany ....... 2732743

[51] Int. Cl.² ............................................. G01N 27/58
[52] U.S. Cl. ................................................. 204/195 S
[58] Field of Search ............................ 204/195 S, 1 S

[56] References Cited

U.S. PATENT DOCUMENTS

| | | | |
|---|---|---|---|
| 2,030,937 | 2/1936 | Reichmann | 123/145 A |
| 2,898,571 | 8/1959 | Moule et al. | 338/238 |
| 3,252,122 | 5/1966 | Baxter | 338/271 |
| 3,546,086 | 12/1970 | Sayles | 204/195 S |
| 3,844,920 | 10/1974 | Burgett et al. | 204/195 S |
| 3,915,828 | 10/1975 | Cleary et al. | 204/195 S |
| 3,928,161 | 12/1975 | McIntyre et al. | 204/1 S |
| 3,999,947 | 12/1976 | Mihara et al. | 23/254 E |
| 4,129,099 | 12/1978 | Howarth | 204/195 S |
| 4,129,491 | 12/1978 | Obiaya | 204/195 S |

FOREIGN PATENT DOCUMENTS 2304464 8/1974 Fed. Rep. of Germany ....... 204/195 S

Primary Examiner—G. L. Kaplan
Attorney, Agent, or Firm—Frishauf, Holtz, Goodman & Woodward

[57] ABSTRACT

An electrical heating element 35, 35' is located in a thin walled, closed metal tube or sleeve 37, 37' which is packed with a packing material 38, 38' of good heat conductive, insulating properties; the electrical heating element is a spirally wound resistance heater embedded in the insulating packing. A solid electrolyte body 11, 68 surrounds at least a portion of the thin walled metal sleeve and is positioned in heat exchange relation therewith. The solid electrolyte body may be a closed tube 11 or may be applied as a ring element 68 over the thin walled metal tube with an insulating material layer 66 interposed.

8 Claims, 3 Drawing Figures